United States Patent [19]

Frick et al.

[11] Patent Number: 4,657,921
[45] Date of Patent: Apr. 14, 1987

[54] 2,2-DIPHENYL-1-FLUORO-1-AZOLYLE-THANEMICROBICIDES

[75] Inventors: Willy Frick, Pfeffingen; Alfred Meyer; Robert Nyfeler, both of Basel, all of Switzerland

[73] Assignee: Ciba-Geigy Corporation, Ardsley, N.Y.

[21] Appl. No.: 734,643

[22] Filed: May 16, 1985

[30] Foreign Application Priority Data

May 23, 1984 [CH] Switzerland ............... 2534/84

[51] Int. Cl.$^4$ .................. A01N 43/50; A01N 43/653; C07D 233/56; C07D 249/08
[52] U.S. Cl. .................. 514/383; 514/396; 514/399; 548/262; 548/335
[58] Field of Search ............... 548/262, 335; 514/383, 514/396, 399

[56] References Cited

U.S. PATENT DOCUMENTS 4,213,990  7/1980  Frick et al. ............... 424/269

FOREIGN PATENT DOCUMENTS 3121676  12/1982  Fed. Rep. of Germany .

OTHER PUBLICATIONS

Hertenstein et al., Chemical Abstracts, vol. 98(1982), 107301z.
Sumitomo Chem. Co., Chemical Abstracts, vol. 96(1981), 181,282u.

*Primary Examiner*—Richard L. Raymond
*Attorney, Agent, or Firm*—Edward McC. Roberts; Meredith C. Findlay

[57] ABSTRACT

There are described novel 1-fluoro-1-azolyl-2,2-diaryle-thane derivatives of the general formula I

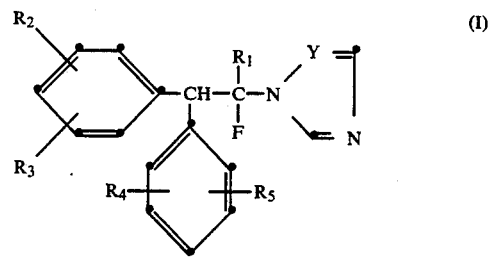

wherein
Y is —CH= or —N=,
$R_1$ is hydrogen or $C_1$-$C_3$-alkyl, and
$R_2$, $R_3$, $R_4$ and $R_5$ independently of one another are each hydrogen, halogen, methyl, methoxy, $CF_3$, $OCF_3$, $OCHF_2$, cyano, and/or phenoxy which is unsubstituted or substituted by fluorine, chlorine and/or bromine;

including the acid addition salts and metal complexes thereof.

Also the production of these substances as well as their microbicidal action and their use in various fields of application are described.

7 Claims, No Drawings

2,2-DIPHENYL-1-FLUORO-1-AZOLYLE-THANEMICROBICIDES

The present invention relates to novel 1-halo-1-azolyl-2,2-diarylethane derivatives which have antimicrobial activity and are useful in the treatment of e.g. fungal infections in warm-blooded animals, including humans, and as agricultural (including horticultural) microbicides. The invention relates also to the production of these substances as well as to microbicidal compositions containing as active ingredient at least one of these compounds. Further subject matter of the invention is the use of the active substances for controlling harmful microorganisms, particularly fungi.

According to the invention there are provided compounds of the formula I

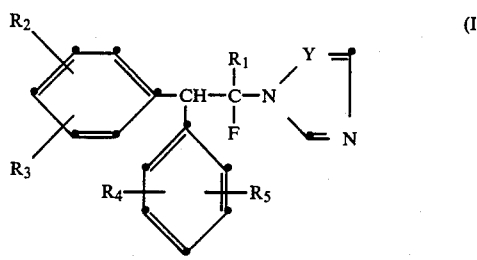

and their agriculturally and pharmaceutically acceptable salts, wherein

Y is $-CH=$ or $-N=$, $R_1$ is hydrogen or $C_1$–$C_3$-alkyl, and $R_2$, $R_3$, $R_4$ and $R_5$ independently of one another are each hydrogen, halogen, methyl, methoxy, $CF_3$, $OCF_3$, $OCHF_2$, cyano, and/or phenoxy which is unsubstituted or substituted by fluorine, chlorine and/or bromine; and include also the agriculturally useful metal complexes.

Halogen is fluorine, chlorine, bromine and iodine, and $C_1$–$C_3$-alkyl is methyl, ethyl, propyl and isopropyl.

Examples of salt-forming acids are inorganic acids: hydrohalic acid, such as hydrofluoric acid, hydrochloric acid, hydrobromic acid or hydriodic acid, as well as sulfuric acid, phosphoric acid, phosphorous acid or nitric acid; and organic acids, such as acetic acid, trifluoroacetic acid, trichloroacetic acid, propionic acid, tartaric acid, glycolic acid, thiocyanic acid, lactic acid, succinic acid, citric acid, benzoic acid, cinnamic acid, oxalic acid, formic acid, benzenesulfonic acid, p-toluene-sulfonic acid, methanesulfonic acid, salicyclic acid, p-aminosalicylic acid, 2-phenoxybenzoic acid or 2-acetoxybenzoic acid. These acids are added by methods known per se to the free compounds of the formula I and subsequent filtration of the desired salt or evaporation of the solvent used.

Metal complexes of the formula I consist of the basic organic molecule and an inorganic or organic metal salt, for example: the halides, nitrates, sulfates, phosphates or acetates, of manganese, iron, cobalt, nickel, zirconium, copper and zinc.

The compounds of the formula I are stable at room temperature. They can be used in agriculture or in related fields in a preventive and curative manner for combating phytopathogenic microorganisms, the preferred compounds being the triazolylmethyl derivatives embraced by the formula I. The active substances of the formula I according to the invention are characterised, within a wide range of applied concentrations, by very good fungicidal activity, and by their great ease of application.

The following groups of substances are preferred by virtue of their pronounced microbicidal action:

(a) compounds of the formula I wherein Y is $-N=$, $R_1$ is hydrogen or $C_1$–$C_3$-alkyl, $R_2$ is hydrogen, 2—F, 2—Cl, 2—$CH_3$, 2—$C_2H_5$ or 2—$CF_3$, $R_3$ is hydrogen, 4—Cl, 4—$OCHF_2$, 4-phenoxy or 4-(4'-halophenoxy), $R_4$ is hydrogen, 2—F, 2—Cl, 2—$CH_3$, 2—$C_2H_5$ or 2—$CH_3$, and $R_5$ is hydrogen, 4—Cl, 4—$OCHF_2$, 4—F, 4-phenoxy or 4-(4'-halophenoxy); and (b) compounds of the formula I wherein Y is $-N=$, $R_1$ is hydrogen, $R_2$ is hydrogen, 2—Cl or 2—$CH_3$, $R_3$ is p-halophenoxy, $R_4$ is hydrogen, and $R_5$ is p-halogen.

Particularly preferred individual substances are for example the following compounds of the formula I:

1-fluoro-1-(1H-1,2,4-triazol-1-yl)-2-(2,4-dichlorophenyl)-2-(4-fluorophenyl)ethane,
1-fluoro-1-(1H-1,2,4-triazol-1-yl)-1-methyl-2-(2,4-dichlorophenyl)-2-(4-fluorophenyl)ethane,
1-fluoro-1-(1H-1,2,4-triazolyl-1-yl)-1-ethyl-2-(2,4-dichlorophenyl)-2-(4-fluorophenyl)ethane,
1-fluoro-1-(1H-imidazol-1-yl)-2-(2,4-dichlorophenyl)-2-(4-fluorophenyl)ethane,
1-fluoro-1-(1H-1,2,4-triazol-1-yl)-2-bis(4-chlorophenyl)ethane,
1-fluoro-1-(1H-1,2,4-triazol-1-yl)-2-(4-chlorophenyl)-2-(4-fluorophenyl)ethane,
1-fluoro-1-(1H-1,2,4-triazol-1-yl)-2-(4-chlorophenyl)-2-(2-fluorophenyl)ethane, and
1-fluoro-1-(1H-1,2,4-triazol-1-yl)-2-phenyl-2-(2,4-dichlorophenyl)ethane.

The compounds of the formula I can be obtained by reacting an alcohol of the formula II

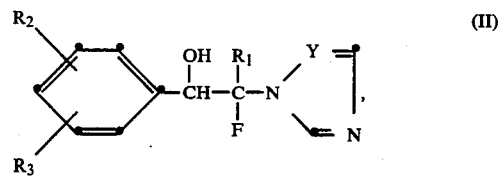

in the presence of an acid or Lewis acid, with a benzene derivative of the formula III

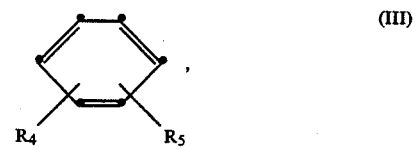

wherein $R_1$, $R_2$, $R_3$, $R_4$, $R_5$ and Y have the meanings defined under the formula I. The reaction is advantageously performed within the temperature range of $-20°$ to $+80°$ C., preferably $-10°$ to $+30°$ C., and particularly preferably $-5°$ to $+20°$ C.

The solvent preferably used is an excess of the reactant of the formula III. There can be present as inert diluents in the reaction for example nitrobenzene or aliphatic hydrocarbons, such as cyclohexane, hexane, and so forth. Suitable acids are for example concentrated mineral acids, such as sulfuric acid, phosphoric acid or hydrohalic acids (HCl, HF or HBr), and sulfonic acids, such as benzenesulfonic acid or p-toluenesulfonic acid. Suitable Lewis acids are for example the halides of boron, aluminium, zinc, antimony, mercury, copper, silver or titanium (BF$_3$, ZnCl$_2$, AlCl$_3$, FeCl$_3$, SbCl$_5$, SnCl$_4$, TiCl$_4$, ZnCl$_2$, and the like). Concentrated H$_2$SO$_4$ and AlCl$_3$ are especially preferred.

The starting compounds of the formula II are obtainable from the basic α,α-dihaloketones of the formula IV

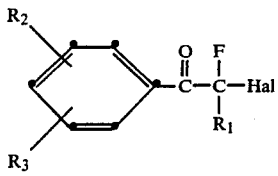
(IV)

by reaction with an azole of the formula V

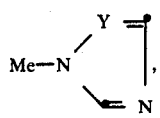
(V)

wherein R$_1$, R$_2$, R$_3$ and Y have the meanings defined under the formula I, Hal is halogen, preferably chlorine or bromine, and Me is hydrogen or preferably an alkali metal kation or alkaline-earth metal kation, particularly Na$^+$ or K$^+$. Reactions of this type—replacement of a halogen atom by an azole ring—are sufficiently well known from the literature.

The compounds of the formula IV are obtainable by halogenation of the known basic α-haloketones of the formula VI

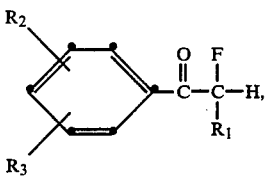
(VI)

wherein the substituents are as defined under the formula I [F. Bergmann et al., J. Am. Chem. Soc. 79, 4178 (1957)].

The described production process forms a part of the present invention.

The compounds of the formula I contain, in the position adjacent to the azole group, always an asymmetric *C atom, and can therefore be present in two enantiomeric forms. In the production of these substances, there is generally formed a mixture of both enantiomers. This can be separated, in the customary manner, for example by fractional crystallisation of salts with optically active strong acids, into the pure optical antipodes. The two enantiomers can exhibit different biological activities. In the cases in which R$_2$ and R$_3$ have meanings different from R$_4$ and R$_5$, there occurs, adjacent to the two phenyl rings, a further asymmetric centre, which results in the existence of diastereoisomeric mixtures (threo and erythro forms). The disastereoisomers can be resolved by means of the customary physical methods.

The present invention relates to all pure enantiomers or diastereoisomers or mixtures thereof with one another.

It has been established that, surprisingly, compounds of the formula I exhibit, for practical purposes, a very favourable microbicidal spectrum against fungi and bacteria. They have very advantageous curative, preventive and systemic properties, and can be used for the protection of cultivated plants. The microorganisms occurring on plants or on parts of plants (fruit, blossom, foliage, stalks, tubers or roots) of various cultivated crops can be inhibited or destroyed with the active substances of the formula I, and also parts of plants subsequently growing remain preserved from such microorganisms.

The active substances of the formula I are effective against the phytopathogenic fungi belonging to the following classes: Ascomycetes (for example: Venturia, Podosphaera, Erysiphe, Monilinia and Uncinula); Basidiomycetes (for example the species: Hemileia, Rhizoctonia and Puccinia); Fungi imperfecti (for example: Botrytis, Helmintosporium, Fusarium, Septoria, Cercospora and Alternaria). Furthermore, the compounds of the formula I have a systemic action. They can be used also as dressing agents for the treatment of seed (fruits, tubers and grain) and of plant cuttings to protect them from fungus infections, and also against phytopathogenic fungi occurring in the soil. The active substances according to the invention are characterised also by particularly high tolerance to plants.

The invention relates also to microbicidal compositions as well as to the use of the compounds of the formula I for controlling pathogenic microorganisms, especially fungi which damage plants, and for preventing an infestation of plants by fungi.

Within the scope of this invention, target crops with respect to the range of indications disclosed herein include for example the following species of cultivated plants: cereals: (wheat, barley, rye, oats, rice, sorghum and related cereals); beet: (sugar beet and fodder beet); pomaceous fruit, stone fruit and soft fruit: (apples, pears, plums, peaches, almonds, cherries, strawberries, raspberries and blackberries); legumes: (beans, lentils, peas and soya-bean); oil plants: (rape, mustard, poppy, olives, sunflowers, coco, castor-oil plants, cocoa and groundnuts); Cucurbitacea: (pumpkins, cucumbers and melons); fibre plants: (cotton, flax, hemp and jute); citrus fruits: (oranges, lemons, grapefruit and mandarins); varieties of vegetables: (spinach, lettuce, asparagus, varieties of cabage, carrots, onions, tomatoes, potatoes and paprika); laurel plants: (avocado, cinnamon and camphor); or plants such as maize, tobacco, nuts, coffee, sugar beet, tea, grapevines, hops, bananas and natural rubber plants, as well as ornamental plants (flowers, shrubs, deciduous trees and conifers). This list constitutes no limitation.

Active substances of the formula I are customarily used in the form of compositions, and can be applied, simultaneously or successively, with further active substances to the area or plants to be treated. These further active substances can be fertilisers, trace-element agents or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

Suitable carriers and additives can be solid or liquid and they correspond to the substances customarily employed in formulation practice, for example: natural or regenerated mineral substances, solvents, dispersing agents, wetting agents, adhesives, thickeners, binders or fertilisers.

The compounds of the formula I are used either in an unmodified form or preferably together with auxiliaries customarily employed in formulation practice, and are thus processed in a known manner for example into the form of emulsion concentrates, brushable pastes, directly sprayable or dilutable solutions, diluted emulsions, wettable powders, soluble powders, dusts or granulates, and also encapsulations in for example polymeric substances. The application processes and likewise the type of composition are selected to suit the objectives to be achieved and the given conditions. In agriculture, favourable applied amounts are in general between 50 g and 5 kg of active substance (AS) per hectare, preferably between 100 g and 2 kg of AS per hectare, and in particular between 100 g and 600 g of AS per hectare.

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ether, ketones, such as cyclohexanone, strongly polar solvents, such as N-methyl-2-pyrrolidone, dimethyl sulfoxide or dimethyl formamide, and also optionally epoxidised vegetable oils, such as epoxidised coconut oil or soybean oil; or water.

Particularly advantageous additives which facilitate application and which can effect a considerable reduction in the amount of active substance applied are moreover natural (animal or vegetable) or synthetic phospholipides from the series of kephalins and lecithins, for example: phosphatidyl ethanolamine, phosphatidyl serine, phosphatidyl glycerol or lysolecithin.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

The tensides customarily used in formulation practice are described, inter alia, in the following publications:
"Mc Cutcheon's Detergents and Emulsifiers Annual",
  MC Publishing Corp., Ridgewood, N.J., 1981;
Dr. Helmut Stache, "Tensid-Taschenbuch" (Tenside Handbook), Carl Hanser Verlag, Munich/Vienna, 1981; and
M. and J. Ash, "Encyclopedia of Surfactants", Vol. I–III, Chemical Publishing Co., New York, 1980–1981.

The agrochemical preparations contain as a rule 0.1 to 99%, particularly 0.1 to 95%, of active ingredient of the formula I, 99.9 to 1%, especially 99.8 to 5%, of a solid or liquid additive, and 0 to 25%, in particular 0.1 to 25%, of a tenside. Whereas commercial products are preferably in the form of concentrated compositions, the preparations employed by the end-user are as a rule diluted.

The following Examples serve to further illustrate the invention without limiting the scope thereof. Temperatures are in degrees Centigrade, and percentages and 'parts' relate to weight.

PRODUCTION EXAMPLES

Example P1

Production of

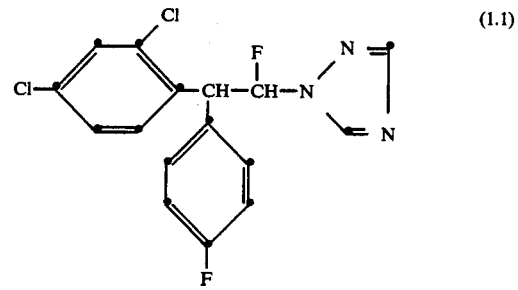

(1.1)

1-Fluoro-1-(1H-1,2,4-triazol-1-yl)-2-(2,4-dichlorophenyl)-2-(4-fluorophenyl)ethane (a) Production of the starting product

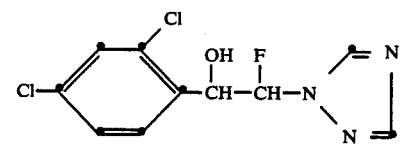

1-(2,4-Dichlorophenyl)-2-fluoro-2-(1H-1,2,4-triazol-1-yl)ethanol

To a suspension of 2.4 g of 1-(2,4-dichlorophenyl)-2-fluoro-2-(1H-1,2,4-triazol-1-yl)ethanone in 9.5 ml of methanol and 0.5 ml of water is added at 5°–10° C., with stirring, 0.12 g of sodium borohydride, and the resulting mixture is stirred firstly for 1 hour at 0°–5° C. and then for 2 hours at room temperature, in the course of which a clear solution gradually forms. This solution is then poured into ice-water, and the mixture is extracted twice with dichloromethane. The combined extracts are dried over sodium sulfate, filtered, and concentrated by evaporation. The residue is distilled under high vacuum to obtain the above alcohol as a diastereoisomeric mixture; b.p. of the crude product: 150°–160° C./0.07 mbar. Crystallisation from diethyl ether/diisopropyl ether yields the purified diastereoisomeric mixture in the form of beige crystals; melting range 103°–112° C.

(b) Production of the final product 276 g of 1-(2,4-dichlorophenyl)-2-fluoro-2-(1H-1,2,4-triazol-1-yl)ethanol are introduced, with vigorous stirring, into a mixture, cooled to 0° C., of 1 liter of 98% $H_2SO_4$ and 300 ml of fluorobenzene in such a manner that the internal temperature does not exceed +10° C. The reaction mixture is subsequently stirred at room temperature for a further 6 hours; it is then poured onto about 1.5 kg of ice, and extracted three times with 300 ml of methylene chloride each time. The combined extracts are washed neutral with water, dried over sodium sulfate, filtered, and excess solvent and fluorobenzene are distilled off. The resulting light-brown resin is subjected to short-path distillation at 0.05 mbar and 160° C. (bath temperature). There are thus obtained 300 g (yield about 85%) of a light-coloured, glass-like substance. This glass can be caused to crystallise by means of cyclohexane/diethyl ether; melting range 96°–104°

C. The analytical data show that the product obtained is a diastereoisomeric mixture of the compound No. 1.1.

By a procedure analogous to that described, there can be produced also the compounds of the formula I listed in the following Table 1, which compounds, except where otherwise stated, are obtained as diastereoisomeric mixtures.

TABLE 2

Compounds of the formula

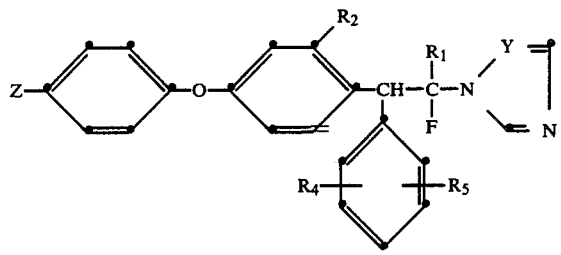

| Comp. No. | $R_1$ | $R_2$ | Z | $R_4$ | $R_5$ | Y | Physical constants [°C.] |
|---|---|---|---|---|---|---|---|
| 2.1 | H | H | Cl | H | H | N | $n_D^{50}$ 1.5758 |
| 2.2 | $CH_3$ | H | Cl | H | H | N | |
| 2.3 | $CH_3$ | H | Cl | H | 4-F | N | |
| 2.4 | $CH_3$ | H | Cl | H | 4-F | CH | |
| 2.5 | H | H | Br | H | 4-Cl | N | |
| 2.6 | H | H | F | 2-Cl | 4-Cl | N | |
| 2.7 | H | $CH_3$ | Cl | H | H | N | |
| 2.8 | $CH_3$ | $CH_3$ | Cl | H | H | N | m.p. 125–127° |

TABLE 1

Compounds of the formula I

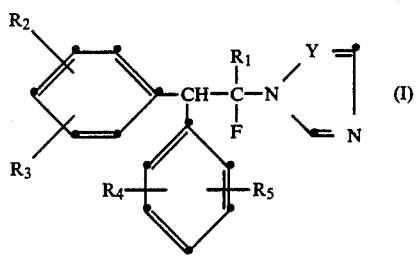

| Comp. No. | $R_1$ | $R_2$ | $R_3$ | $R_4$ | $R_5$ | Y | Physical constants [°C.] |
|---|---|---|---|---|---|---|---|
| 1.1 | H | 2-Cl | 4-Cl | H | 4-F | N | m.p. 96–104° |
| 1.2 | H | 2-Cl | 4-Cl | H | 4-F | CH | oil |
| 1.3 | $CH_3$ | 2-Cl | 4-Cl | H | 4-F | N | m.p. 101–103° |
| 1.4 | $C_2H_5$ | 2-Cl | 4-Cl | H | 4-F | N | m.p. 99–101° |
| 1.5 | H | 2-Cl | 4-Cl | H | H | N | $n_D^{50}$ 1.5764 |
| 1.6 | $CH_3$ | 2-Cl | 4-Cl | H | H | N | m.p. 84–86° |
| 1.7 | H | 2-Cl | 4-Cl | 2-Cl | H | N | |
| 1.8 | $CH_3$ | 2-Cl | 4-Cl | 2-Cl | H | N | |
| 1.9 | H | 2-Cl | 4-Cl | H | 4-Cl | N | $n_D^{50}$ 1.5910 |
| 1.10 | $CH_3$ | 2-Cl | 4-Cl | H | 4-Cl | N | $n_D^{50}$ 1.5795 |
| 1.11 | $C_2H_5$ | 2-Cl | 4-Cl | H | 4-Cl | N | |
| 1.12 | $CH_3$ | 2-Cl | 4-Cl | H | 4-Br | N | m.p. 107–108° |
| 1.13 | H | 2-Cl | 4-Cl | 2-F | H | N | |
| 1.14 | H | H | 4-Cl | 2-F | H | N | $n_D^{50}$ 1.5556 |
| 1.15 | $C_3H_7$—n | 2-Cl | 4-Cl | 2-F | H | N | |
| 1.16 | H | 2-Cl | 4-Cl | 2-$OCHF_2$ | H | N | |
| 1.17 | H | 2-Cl | 4-Cl | H | 4-$OCF_3$ | N | |
| 1.18 | H | 2-Cl | H | H | 4-Cl | N | |
| 1.19 | $CH_3$ | 2-Cl | H | H | 4-Cl | N | |
| 1.20 | H | 2-Cl | H | H | 4-F | N | |
| 1.21 | H | 2-Cl | H | H | 4-F | CH | |
| 1.22 | $CH_3$ | 2-Cl | H | H | 4-F | N | |
| 1.23 | H | 2-F | H | H | 4-F | N | $n_D^{50}$ 1.5395 |
| 1.24 | $CH_3$ | 2-F | H | H | 4-F | N | |
| 1.25 | $C_2H_5$ | 2-F | H | H | 4-F | N | |
| 1.26 | H | H | 4-Cl | H | 4-Cl | N | m.p. 74–75° |
| 1.27 | $CH_3$ | H | 4-Cl | H | 4-Cl | N | |
| 1.28 | H | H | 4-Cl | H | 4-F | N | $n_D^{50}$ 1.5630 |
| 1.29 | H | 2-$CH_3$ | 4-Cl | H | 4-Cl | N | |
| 1.30 | $CH_3$ | 2-$CH_3$ | 4-Cl | H | 4-Cl | N | |
| 1.31 | H | 2-Cl | 4-$OCHF_2$ | H | 4-Cl | N | |
| 1.32 | H | H | 4-Cl | H | 4-Br | N | m.p. 79–80° |
| 1.33 | H | 2-$CF_3$ | H | H | 4-Cl | N | |
| 1.34 | H | 2-Cl | 4-Cl | 2-$CF_3$ | H | N | |
| 1.35 | $CH_3$ | 2-Cl | 4-Cl | H | 4-CN | N | |

TABLE 2-continued

Compounds of the formula

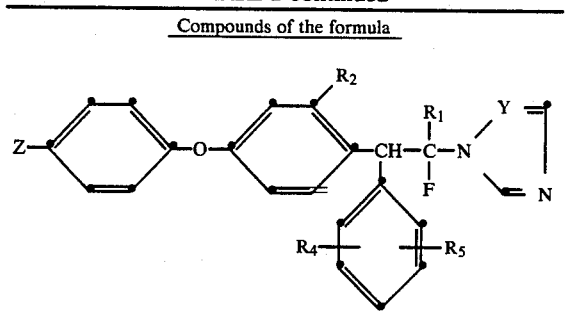

| Comp. No. | R1 | R2 | Z | R4 | R5 | Y | Physical constants [°C.] |
|---|---|---|---|---|---|---|---|
| 2.9 | H | CH3 | Cl | H | 4-F | N | m.p. 82-84° |
| 2.10 | CH3 | CH3 | Cl | H | 4-F | N | m.p. 95-96° |
| 2.11 | C2H5 | CH3 | Cl | H | 4-F | N | |
| 2.12 | H | CH3 | Cl | H | 4-Cl | N | |
| 2.13 | CH3 | CH3 | Cl | H | 4-Cl | N | |
| 2.14 | H | C2H5 | H | H | 4-F | N | |
| 2.15 | CH3 | C2H5 | H | H | 4-F | N | |
| 2.16 | H | H | H | H | H | N | |
| 2.17 | CH3 | H | H | H | H | N | |
| 2.18 | H | Cl | H | H | 4-F | N | |
| 2.19 | CH3 | Cl | H | H | 4-F | N | |
| 2.20 | H | Cl | Cl | H | H | N | |
| 2.21 | H | Cl | Cl | H | 4-F | N | $n_D^{50}$ 1.5761 |
| 2.22 | CH3 | Cl | Cl | H | 4-F | N | |
| 2.23 | C2H5 | Cl | Cl | H | 4-F | N | |
| 2.24 | H | H | Cl | H | 4-Cl | N | m.p. 95-97° |
| 2.25 | CH3 | Cl | Cl | H | 4-Cl | N | |
| 2.26 | H | Cl | F | H | 4-Cl | N | |

Formulation Examples for active ingredients of the formula I (%=percent by weight)

| F1. Solutions | (a) | (b) | (c) | (d) |
|---|---|---|---|---|
| active ingredient from the Tables | 80% | 10% | 5% | 95% |
| ethylene glycol-monomethyl ether | 20% | — | — | — |
| polyethylene glycol (MW 400) | — | 70% | — | — |
| N—methyl-2-pyrrolidone | — | 20% | — | — |
| epoxidised coconut oil | — | — | 1% | 5% |
| ligroin (boiling limits 160-190° C.) | — | — | 94% | — |

(MW = molecular weight)

The solutions are suitable for application in the form of very small drops.

| F2. Granulates | (a) | (b) |
|---|---|---|
| active ingredient from the Tables | 5% | 10% |
| kaolin | 94% | — |
| highly dispersed silicic acid | 1% | — |
| attapulgite | — | 90% |

The active ingredient is dissolved in methylene chloride; the solution is sprayed onto the carrier, and the solvent is subsequently evaporated off in vacuo.

| F3. Dusts | (a) | (b) |
|---|---|---|
| active ingredient from the Tables | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

| F4. Wettable powders | (a) | (b) | (c) |
|---|---|---|---|
| active ingredient from the Tables | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with the additives, and the mixture is thoroughly ground in a suitable mill. Wettable powders which can be diluted with water to give suspensions of the required concentration are obtained.

| F5. Emulsion concentrate | |
|---|---|
| active ingredient from the Tables | 10% |
| octylphenol polyethylene glycol ether (4-5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| F6. Coated granulate | |
|---|---|
| active ingredient from the Tables | 3% |
| polyethylene glycol (M.W. 200) | 3% |
| kaolin | 94% |

(M.W. = molecular weight)

The finely ground active ingredient is evenly applied, in a mixer, to the kaolin moistened with polyethylene glycol. Dustfree coated granules are obtained in this manner.

BIOLOGICAL EXAMPLES

Example B1

Action against *Puccinia graminis* on wheat
Residual-protective action

Six days after being sown, wheat plants are sprayed with a spray liquor prepared from wettable powder of the active ingredient (0.02% of active ingredient). After 24 hours, the treated plants are infested with a uredospore suspension of the fungus. After an incubation time of 48 hours at about 20° C. with 95-100% relative humidity, the infested plants are kept in a greenhouse at about 22° C. An assessment of the development of rust pustules is made 12 days after infestation.

Untreated but infested control plants display a level of Puccinia infection of 100%. Compounds from Tables 1 and 2 exhibit a good action against Puccinia fungi. Among other compounds giving good results, the compounds Nos. 1.1, 1.3, 1.4, 1.5, 1.10 and 1.28 reduce Puccinia infection to 0 to 5%.

Example B2

Action against *Cercospora arachidicola* on groundnut plants (a) Residual-protective action Groundnut plants 10–15 cm in height are sprayed with a spray liquor produced from wettable powder of the active ingredient (0.02% of active ingredient); and 48 hours later they are infested with a conidiospore suspension of the fungus. The infested plants are incubated for 72 hours at about 21° C. with a high relative humidity, and are subsequently kept in a greenhouse until the typical leaf spots have appeared. The assessment of the fungicidal action is made 12 days after infestation, and is based on the number and size of the occurring spots.

(b) Systemic action

A spray liquor prepared from wettable powder of the active ingredient (0.06% of active ingredient, relative to the volume of soil) is poured onto the soil of groundnut plants 10–15 cm in height. After 48 hours, the treated plants are infested with a conidiospore suspension of the fungus, and are subsequently incubated for 72 hours at about 21° C. with high relative humidity. The plants are then kept in a greenhouse, and an assessment of the extent of fungus infection is made after 11 days.

Compared with untreated but infested control plants (number and size of spots=100%), groundnut plants which have been treated with the active ingredients from Tables 1 and 2 exhibit a greatly reduced level of Cercospora infection. Thus, the compounds Nos. 1.1, 1.3, 1.4, 1.5, 1.14, 1.26, 1.28, 2.1, 2.8, 2.9 and 2.24 prevent the occurrence of spots in the above tests almost completely (0–10%).

Example B3

Action against *Erysiphae graminis* on barley (a) Residual-protective action

Barley plants about 8 cm in height are sprayed with a spray liquor prepared from wettable powder of the active ingredient (0.02% of active ingredient). After 3–4 hours, the treated plants are dusted with conidiospores of the fungus. The infested barley plants are kept in a greenhouse at about 22° C., and the extent of fungus infection is assessed after 10 days.

(b) Systemic action

A spray liquor prepared from wettable powder of the active ingredient (0.006% of active ingredient, relative to the volume of soil) is poured onto the soil of barley plants about 8 cm in height. Care is taken to ensure that the spray liquor does not come into contact with the parts of the plants above the soil. After 48 hours, the treated plants are dusted with conidiospores of the fungus. The infested barley plants are kept in a greenhouse at about 22° C., and an assessment of the extent of fungus infection is made after 10 days.

Compounds of the formula I exhibit a good action against Erysiphe fungus. Untreated but infested control plants display a level of Erysiphe infection of 100%. Among other effective compounds shown in Tables 1 and 2, the compounds Nos. 1.1, 1.3, 1.4, 1.5, 1.6, 1.9, 1.10, 1.12, 1.14, 1.23, 1.26, 1.28, 1.32, 2.1, 2.8, 2.9, 2.10, 2.21 and 2.24 reduce fungus infection on barley to 0 to 5%.

Example B4

Residual-protective action against *Venturia inaequalis* on apple shoots

Apple seedlings having 10–20 cm long fresh shoots are sprayed with a spray liquor prepared from wettable powder of the active ingredient (0.06% of active ingredient). The treated plants are sprayed after 24 hours with a conidiospore suspension of the fungus. The plants are then incubated for 5 days with 90–100% relative humidity, and for a further 10 days they are kept at 20°–24° C. in a greenhouse. The extent of scab infection is assessed 15 days after infestation.

Compounds from Tables 1 and 2 bring about a clear reduction of infection. Thus, the compounds Nos. 1.1, 1.3, 1.4, 1.5, 1.6, 1.9, 1.10, 1.12, 1.14, 1.23, 1.26, 1.28, 1.32; 2.1, 2.8, 2.9, 2.10, 2.21 and 2.24 prevent fungus infection almost completely (0–5%). Untreated but infested shoots suffer a 100% level of Venturia infection.

Example B5

Action against *Botrytis cinerea* on beans Residual protective action

Bean plants about 10 cm in height are sprayed with a spray liquor prepared from wettable powder of the active ingredient (0.02% of active ingredient). The plants are infested after 48 hours with a conidiospore suspension of the fungus. The extent of fungus infection is assessed after incubation of the infested plants for 3 days at 21° C. with 95–100% relative humidity.

The Botrytis infection of untreated but infested bean plants amounts to 100%. The level of infection after treatment with any one of the compounds of the formula I is <20%; and in the case of treatment with Compounds Nos. 1.1, 1.5, 1.28 and other compounds there occurs virtually no infection (0–5%).

To be emphasised is the excellent action of the compounds of the formula I and salts thereof against candidiasis and other infections caused by fungi, in particular dermatophyton, such as Trichophyton, Blastomyces, Torulopsis, Microsporum, Sporotrichum, Aspergillus, Staphylococcus, and others. In suitable formulations, the preparation can be solid, semisolid or liquid, and can be in the form of tablets, capsules, powders, suppositories, flowing solutions, suspensions, creams, lotions, gels, ointments, and the like. Nontoxic carriers which are customarily used for solid formulations are for example: tricalcium phosphate, calcium carbonate, kaolin, bentonite, talcum, gelatine, lactose, starch, and so forth; and for semisolid formulations for example: polyalkylene glycols, vaseline, petrolatum and other cream bases; and for liquid preparations for example: water, oils of vegetable origin, and low-boiling solvents, such as isopropanol. By animals are understodd warm-blooded animals, preferably ungulate animals, e.g. ruminants, poultry and pet animals.

For the aforementioned application purposes, the described compounds of the formula I and their antimicrobial acid addition salts, or preparations containing such active ingredients, can be administered to humans and animals by conventional methods, for example locally, orally, parenterally, and so forth. Local administration embraces also intravaginal administration.

In the case of such treatments, a surface area which is infested by fungus or bacterial growth, or which has to be protected against infestation of this kind, can be treated with compounds of the formula I or with antimicrobial acid addition salts thereof, or with preparations containing such active ingredients, for example by dusting, dripping, spraying, rinsing or coating.

For systemic, such as oral or parenteral, administration, it is advantageous, for the attainment of effective results, to administer the active substance in a daily dosage of 1–100 mg/kg of body weight, especially 5–50 mg/kg of body weight, preferably in several doses. Proportionally less active substance is required however for local administration.

Example B6

Determination of fungus inhibitory concentrations (MIC)

36 g of Mycophil agar (consisting of 10 g of peptone, 10 g of dextrose and 16 g of agar) are suspended in 1000 ml of distilled water. In each case, 20 ml of the diluted suspension are placed into Petri dishes (∅ 8.5 cm) and allowed to dry at 35° C. An active-substance solution (solvent: dimethyl sulfoxide) is then applied to each agar plate in the dish by means of a pin of a Steer Applicator, so that there are obtaind active-substance concentrations of 128, 64, 32, 16, 8, 4, 2 and 1 mcg/ml. Each of these plates is subsequently inoculated at various points with the microorganisms (drop size=10 µl, containing $10^3$ organisms).

The incubation at 28° C. lasts 3 days for Candida, and 7 days for all other microorganisms.

The inhibitory concentration (MIC in µg/ml) is tested on the following fungi:

SA = *Staphylococcus aureus* 10 B,
CA = *Candida albicans* ATCC 11651,
TG = *Torulopsis glabrata* K-589,
BD = *Blastomyces derm.* K-1573,
TQ = *Trichophyton quinckeanum* D-24,
MC = *Microsporum canis* ATCC-10214, and
SS = *Sporotrichum schenckii* ATCC-10212.

| Comp. No. | SA | CA | TG | BD | TQ | MC | SS |
|---|---|---|---|---|---|---|---|
| 1.1 | 32 | 4 | 8 | 16 | 4 | 8 | 8 |
| 1.9 | 64 | 2 | 32 | 4 | 2 | 32 | 32 |
| 1.14 | 64 | 4 | 32 | 8 | 2 | 8 | 32 |
| 1.3 | 64 | 16 | 64 | 16 | 2 | 4 | 64 |
| 1.26 | 32 | 4 | 8 | 8 | 1 | 16 | 16 |
| 1.28 | 64 | 4 | 16 | 8 | 1 | 16 | 16 |

What is claimed is:

1. A compound of the formula I

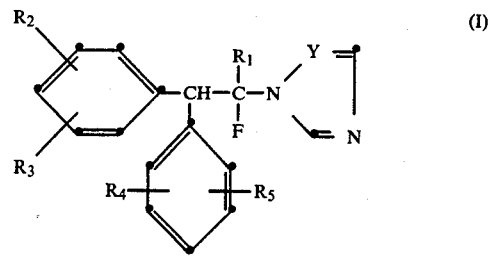

wherein
Y is —CH= or —N=, $R_1$ is hydrogen or $C_1$–$C_3$-alkyl, and $R_2$, $R_3$, $R_4$ and $R_5$ independently of one another are each hydrogen, halogen, methyl, methoxy, $CF_3$, $OCF_3$, $OCHF_2$, cyano, or phenoxy which is unsubstituted or substituted by fluorine, chlorine or bromine.

2. A compound according to claim 1, wherein Y is —N=, $R_1$ is hydrogen or $C_1$–$C_3$-alkyl, $R_2$ is hydrogen, 2—F, 2—Cl, 2—$CH_3$, 2—$C_2H_5$ or 2—$CF_3$, $R_3$ is hydrogen, 4—Cl, 4—$OCHF_2$, 4-phenoxy or 4-(4'-halophenoxy), $R_4$ is hydrogen, 2—F, 2—Cl, 2—$CH_3$, 2—$C_2H_5$ or 2—$CF_3$, and $R_5$ is hydrogen, 4—Cl, 4—$OCHF_2$, 4—F, 4-phenoxy or 4-(4'-halophenoxy).

3. A compound according to claim 1, wherein Y is —N=, $R_1$ is hydrogen, $R_2$ is hydrogen, 2—Cl or 2—$CH_3$, $R_3$ is p-halophenoxy, $R_4$ is hydrogen, and $R_5$ is p-halogen.

4. A compound according to claim 1, selected from the series consisting of:
1-fluoro-1-(1H-1,2,4-triazol-1-yl)-2-(2,4-dichlorophenyl)-2-(4-fluorophenyl)ethane,
1-fluoro-1-(1H-imidazol-1-yl)-2-(2,4-dichlorophenyl)-2-(4-fluorophenyl)ethane,
1-fluoro-1-(1H-1,2,4-triazol-1-yl)-2-bis(4-chlorophenyl)ethane,
1-fluoro-1-(1H-1,2,4-triazol-1-yl)-2-(4-chlorophenyl)-2-(4-fluorophenyl)ethane,
1-fluoro-1-(1H-1,2,4-triazol-1-yl)-2-(4-chlorophenyl)-2-(2-fluorophenyl)ethane, and
1-fluoro-1-(1H-1,2,4-triazol-1-yl)-2-phenyl-2-(2,4-dichlorophenyl)ethane.

5. A microbicidal composition for controlling or preventing an infestation by microorganisms, which composition contains a microbicidally effective amount of a compound according to claim 1 together with a suitable carrier.

6. A method of treating microbial infections which comprises administering an effective amount of a compound according to claim 1 to a warm-blooded animal which is infected or liable to be infected.

7. A method for controlling or preventing an infestation of cultivated plants by phytopathogenic microorganisms, which process comprises applying to the plants or to the locus thereof a microbicidally effective amount of a compound according to claim 1.

* * * * *